United States Patent [19]
Bartz

[11] Patent Number: 5,350,922
[45] Date of Patent: Sep. 27, 1994

[54] UNDERWATER LIGHT SCATTERING SENSOR

[76] Inventor: Robert Bartz, 353356 Riverside Dr., Albany, Oreg. 97321

[21] Appl. No.: 35,256

[22] Filed: Mar. 22, 1993

[51] Int. Cl.⁵ ............................................. G01N 21/49
[52] U.S. Cl. .................... 260/388.5; 250/574; 250/575; 356/338; 356/340; 356/342
[58] Field of Search .................... 356/338, 342, 340; 250/575, 574, 338.5

[56] References Cited

U.S. PATENT DOCUMENTS

| | | | |
|---|---|---|---|
| 3,586,862 | 6/1971 | Topol | 250/574 |
| 3,665,201 | 5/1972 | Shea et al. | 250/574 |
| 3,713,743 | 1/1973 | Simms | 356/338 |
| 3,714,444 | 1/1973 | Carr et al. | 250/574 |
| 4,432,645 | 2/1984 | Früngel | 356/338 |
| 4,497,577 | 2/1985 | Sato et al. | 356/336 |
| 4,841,157 | 6/1989 | Downing, Jr. | 250/574 |
| 5,210,595 | 5/1993 | Devore et al. | 356/442 |

FOREIGN PATENT DOCUMENTS

| | | | |
|---|---|---|---|
| 61-29743 | 2/1986 | Japan | 356/338 |
| 2212261 | 7/1989 | United Kingdom | 356/338 |

OTHER PUBLICATIONS

John P. Downing, R. W. Sternberg and C. R. B. Lister, "New Instrumentation for the Investigation of Sediment Suspension Processes in the Shallow Maring Environment", *Marine Geology*, 1981, vol. 42, pp. 19–34.

Edward S. Fry and Kenneth J. Voss, "Mueller Matrix Measurements of Ocean Water", *SPIE*, vol. 489, Ocean Optics VII (1984), pp. 127–129.

Henri Hodara, "Experimental Results of Small Angle Scattering", *AGARD Lecture Series No. 61 Optics of the Sea*, 1973, pp. 3.4–1 through 3.4–17.

N. G. Jerlov, "Scattering", *Marine Optics*, Elsevier Scientific Publishing Company, Amsterdam, 1976, pp. 13–22, 33–43.

C. A. Moore, R. Honey, D. Hancock, S. Damron, and R. Hilbers, "Development and Use of Computerized Optical Sea–Truth Instrumentation for Lidex–82", SRI International, 1984, pp. 1–66.

Theodore J. Petzold, "Volume Scattering Functions for Selected Ocean Waters", S10, 1972, pp. 3–13, 15–23, 25–27, 29–31, 33–36 and 77–78.

Richard W. Spinrad, "A Calibration Diagram of Specific Team Attenuation", *Journal of Geophysical Research*, vol. 91, No. C6, pp. 7761–7764.

Richard W. Spinrad, J. Ronald Zaneveld, and Hasong Pak, "Volume Scattering Function of Suspended Particulate Matter at Near–Forward Angles: A Comparison of Experimental and Theoretical Values", *Applied Optics*, vol. 17, pp. 1125–1130.

E. M. Thorndike, "A Deep Sea, Photographic Nephelometer", *Ocean Engineering*, Pergamon Press, 1975, vol. 3, pp. 1–15.

John E. Tyler and Roger Howerton, "Instrumentatioln for Measuring the Forward Scattering Coefficient of Sea Water", 1862, pp. 393–395.

Gunnar Kullenberg, "Scattering of Light by Sargasso Sea Water", *Deep–Sea Research*, Pergamon Press, 1968, vol. 15, pp. 423–432.

*Primary Examiner*—Constantine Hannaher
*Attorney, Agent, or Firm*—Donald W. Marks

[57] ABSTRACT

An underwater light scattering sensor includes a light source, light stop and a light detector mounted on a planar support capable of measuring nearly all suspended particle concentrations found in natural waters, 1 μg/l to 3 g/l. The sensor is designed to measure light scattered at nearly all angles, which includes forward scattering, back scattering, and multiple scattering, from suspended particles in water through a very short light path length. The small and simple design of the sensor allows it to be produced at low cost, permitting its use in both expendable and non-expendable applications for the detection or measurement of suspended particulate concentrations in water. The magnitude of the scattered light measured by the sensor is proportional to the suspended particle concentration in water, provided the nature of the particles does not change.

16 Claims, 4 Drawing Sheets

UNDERWATER LIGHT SCATTERING SENSOR

TECHNICAL FIELD

The present invention relates to turbidimeters, nephelometers, or other optical sensors used for the in situ measurement of suspended particle concentrations in a fluid employing scattered light, either visible radiation or near infrared radiation.

BACKGROUND ART

The optical properties of water—light scattering, light absorption, and light transmission—are determined by the nature of the suspended particles in the water such as particle concentration, particle size distribution, index of refraction of the particles, etc. If the nature of the particles does not change significantly in the water column, then there is good correlation between suspended particle concentrations and any of the optical properties. Since light scattering is relatively easy to measure it is widely used to measure suspended particle concentrations in water. Light absorption and light transmission sensors are by comparison relatively complex, large in size, and expensive to produce and for these reasons they are not as widely used as light scattering sensors to measure suspended particle concentrations in water.

Various prior art light scattering sensors have been designed to measure suspended particle concentrations in a fluid or the turbidity of the fluid. These sensors generally use a light source and a light detector appropriately arranged to measure light scattered by particles. However, the dynamic range over which a linear correlation has been obtained with these sensors has been limit to approximately 4 orders of magnitude. The linear measurement of the entire range of natural suspended particle concentrations that can exist in natural waters, which is greater than 6 orders of magnitude extending from approximately 1 microgram per liter ($\mu g/l$) to greater than 1 gram per liter ($g/l$), has never been within the capability of a single design. An optical sensor design with the capability of linearly measuring this full range of suspended particle concentrations is highly desirable, especially if the device can be produced at low cost.

Prior art scattering sensors used to measure the turbidity of a fluid or the suspended particle concentration in a fluid generally fall into three categories: forward scattering, 90° scattering, and back scattering. Forward scattering sensors have been used to measure low particle concentrations in a fluid but they are generally not capable of measuring high concentrations. Scattering sensors employing light scattering in the range of 90°, commonly referred to as nephelometers, have been primarily used to measure the mid-range of suspended particle concentrations in a fluid. Back scattering sensors have been used to measure either low or high suspended particle concentrations, but none have been designed to measure both.

Forward scattering sensors measure light scattered at angles between 0° and 90°. Light scattered from low concentrations of natural particles in water is predominate in the forward direction, because of this forward scattering sensors have been used to measure low suspended particle concentrations in water. However, all prior art forward scattering sensors have used relatively long light path lengths (several centimeters or greater) which has prevented their use for the measurement of very high suspended particle concentrations. This is because the attenuation of light in water increases with both particle concentration and path length. Consequently, relatively long light path length sensors cannot measure high particle concentrations since very little light can reach the detector. Therefore the dynamic range of all prior art forward scattering sensors has been limited to the low end of the naturally occurring range of suspended particle concentrations. Examples of forward scattering sensors are disclosed in Simms U.S. Pat. No. 3,713,743 and Früngel U.S. Pat. No. 4,432,645; and in publications (1) Fry et al., "Mueller Matrix Measurements of Ocean Water", SPIE, vol. 489, Ocean Optics VII (1984), pages 127-129; (2) Hodara, "Experimental Results of Small Angle Scattering", AGARD Lecture Series No. 61 Optics of the Sea, 1973, pages 3.4-1 through 3.4-17; (3) Jerlov, "Scattering", Marine Optics, Elsevier Scientific Publishing Company, Amsterdam, 1976, pages 13-22, 33-43; (4) Petzold, "Volume Scattering Functions for Selected Ocean Waters", SIO, 1972, pages 3-13, 15-23, 25-27, 29-31, 33-36 and 77-78; (5) Spinrad et al., "Volume Scattering Function of Suspended Particulate Matter at Near-Forward Angles: A Comparison of Experimental and Theoretical Values", Applied Optics, Vol. 17, pages 1125-1130; (6) Thomdike, "A Deep Sea, Photographic Nephelometer", Ocean Engineering, Pergamon Progamon Press, 1975, vol. 3, pages 1-15; (7) Tyler et al., "Instrumentation for Measuring the Forward Scattering Coefficient of Sea Water", 1962, pages 393-395; and (8) Kullenberg, "Scattering of Light by Sargasso Sea Water", Deep-Sea Research, Pergamon Press, 1968, Vol. 15, pages 423-432.

Back scattering sensors measure light scattered at angles between 90° C. and 180°. The amount of light scattered at these angles is orders of magnitude less than at forward angles between 0° and 90° for low concentrations of particles in water. Because of this, in the past back scattering devices were primarily used to measure relatively high suspended particle concentrations in water. To increase the sensitivity of backscatter devices to permit the measurement of low particle concentrations in water more light must be radiated into the water and or higher detector sensitivity is required. A prior art back scattering sensor used to measured low particle concentrations has been developed by Moore et al., "Development and Use of Computerized Optical Sea-Truth Instrumentation for Lidex-82", SRI International, 1984, pages 1-66. This device has good sensitivity for the measurement of low particle concentrations but can not measure high concentrations of particles in water because it uses a relatively long light path length in water. Several prior art back scattering sensors have been used to measure very high concentrations of particles in water are exemplified by Downing U.S. Pat. No. 4,841,157, Shea et al. U.S. Pat. No. 3,665,201, Carr et al. U.S. Pat. No. 3,714,444 and Topol U.S. Pat. No. 3,586,862. However, these devices are limited in dynamic range because they do not have adequate sensitivity to measure low suspended particle concentrations in water.

Several other light scattering sensors designed to detect and or measure suspended particles in a fluid or the turbidity of a fluid have been patented or disclosed in the scientific literature. These include forward scattering sensors, backscattering sensors, fixed angle scattering sensors, scanning scattering sensors, and integrating scattering sensors.

None of the prior art light scattering sensors have been designed to combine the advantages of both forward scattering and back scattering in a single sensor design. Multiple scattering must be included as well since for very high suspended particle concentrations in water this is the major light scattering mechanism.

Further the optical design or optical components used or electronic design in the past has limited the performance of light scattering sensors. In general what prevents all prior art designs from achieving a wide dynamic range is a deficiency in one or more of the following parameters: the radiance distribution of the light source, the irradiance distribution of the light detector, the light path length in water, or the optical and or electronic signal to noise ratio. Because of this no prior art sensor exists that can measure the wide range of particle concentrations that can exist in natural waters, which is approximately 1 $\mu g/l$ to more than 1 $g/l$. Furthermore, most prior art scattering sensors are relatively large, complex, and expensive.

SUMMARY OF INVENTION

The present invention is summarized in a light scattering sensor that detects light scattering from particles in water and is used to measure the total suspended particle concentrations in water. A light source and light detector are mounted on a support, and a light stop is mounted between the light source and the light detector to block direct transmission of light from the light source to the light detector. The light scattering sensor is designed to detect forward scattered light, back scattered light and multiple scattered light from suspended particles in water through a very short light path length in water, only a few millimeters for light scattered near the sensor's surface. In addition, very careful attention was given to the sensor electronic and optical design to achieve high signal to noise ratio. The result is a sensor capable of detecting and linearly measuring suspended particle concentrations in water over the range of 1 $\mu g/l$ to 3 $g/l$, permitting a single sensor design to linearly measure nearly the full range of suspended particle concentrations that can exist in natural waters.

An object of the invention is to produce a light scattering sensor design that is capable of linearly measuring suspended particle concentrations in natural waters over six orders of magnitude.

An advantage of the invention is that a single light scattering sensor design can now be used to measure nearly all suspended particle concentrations in natural waters. Linear response over a wide dynamic range, 1 $\mu g/l$ to 3 $g/l$. has been obtained by detecting nearly all light scattered in the direction of the light detector through a very short light path length in water.

Features of the invention include the provision of a sensor that is simple, small, inexpensive and consumes little power permitting its use in both expendable and non-expendable applications for the detection or measurement of nearly all suspended particle concentrations in natural waters.

Additional objects, advantages, and features of the invention will be apparent from the following description of the preferred embodiments taken in conjunction with the accompanying drawings.

DESCRIPTION OF THE PREFERRED EMBODIMENTS

This invention is distinguished from other light scattering sensor inventions in that this light scattering sensor has been designed to measure nearly all light scattered in the direction of the light detector from suspended particles in water, including forward scattered light, backward scattered light and multiple scattered light. In addition to this the sensor has been designed to have the optical signal to noise ratio required to measure very low concentrations of particles in water as well as the required electronic signal to noise ratio. The advantage of this design over other prior art designs is that the linear dynamic range for light scattering sensors used to detect or measure suspended particle concentrations in water has been extended approximately two orders of magnitude.

Figure 1:
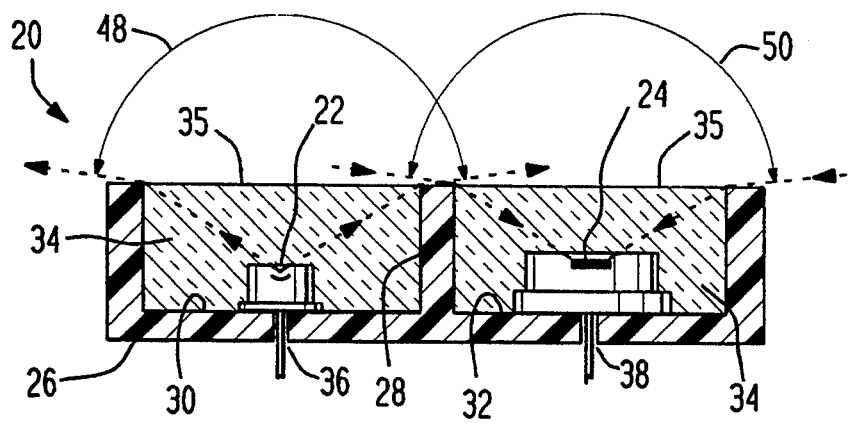
FIG. 1 is a sectional view of a light scattering sensor in accordance with one embodiment of the invention.
Figure 2:
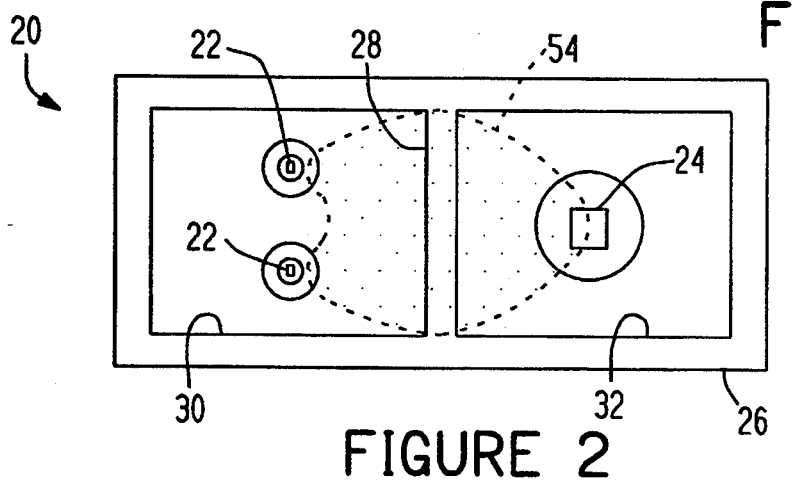
FIG. 2 is a top plan view of the light scattering sensor of FIG. 1.
Figure 3:
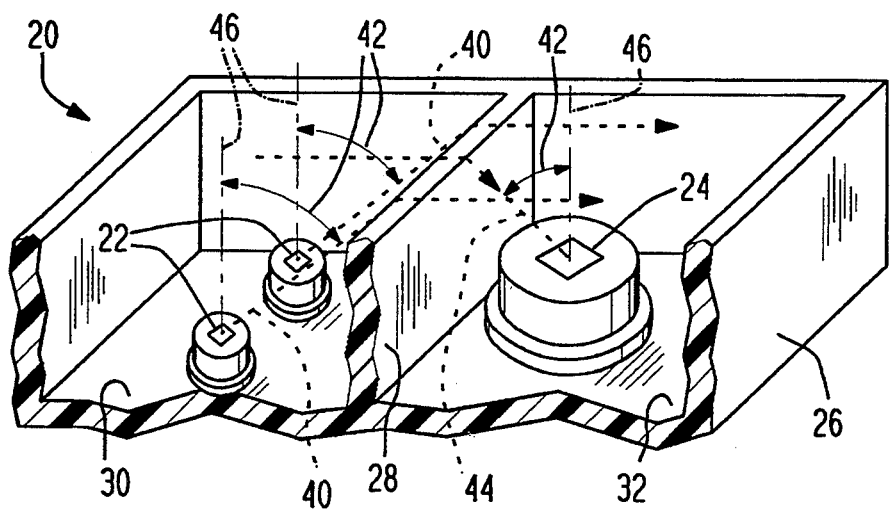
FIG. 3 is an isometric view taken from the upper front right of the light scattering sensor of FIG. 1 with portions broken away.

In accordance with one embodiment of the invention as illustrated in FIGS. 1, 2, and 3, a light scattering sensor indicated generally at 20 for measuring light scattering from suspended particulate matter in water includes one or more light sources 22 and one or more light detectors 24 mounted on a planar support 26 with a light stop 28 blocking any direct radiation path from the light source to the light detector. The light source 22 and the light detector 24 are installed in cavities or enclosures 30 and 32, respectively, arranged side-by-side in a common plane in the support 26 with a common wall between the cavities 30 and 32 forming the light stop 28. The enclosures are encapsulated with an optically clear material, such as optically clear epoxy 34, to form optically clear water proof enclosures. The optically clear material 34 must not extend above the light stop 28 in either cavity to prevent any light leakage from the light source to the light detector. The outer surface 35 of the enclosures extending between the light source 22 and the light detector 24 are generally planar and parallel to the support 26, or cylindrical and parallel to the cylindrical axis that is parallel to the support 25. Apertures 36 and 38 allow for the electrical leads of the source 22 and detector 24 to pass through the support 26. The light source 22, light stop 28 and light detector 24 in this light scattering sensor design are arranged such that the optical signal to noise ratio is very high permitting the measurement of suspended particle concentrations in water as low as 1 µg/l.

As shown in FIG. 3, the light source or sources 22 are located such that a line segment 40 extending from the light source to the top edge of the light stop 28 has an angle 42 equal to the critical angle (angle of total internal reflection) which is determined by the index of refraction of the water and the index of refraction of the optically clear material 34. Likewise, the detector or detectors 24 are located such that a line segment 44 extending from the detector to the top edge of the light stop 28 has the angle 42 equal to the critical angle which is determined by the index of refraction of the water and the index of refraction of the optically clear material 34. Alternatively, the light source 22, the light stop 28 and light detector 24 can be mounted in a variety of ways to produce a sensor that can measure light scattering from suspended particles in water using a short light path in water with an equal or better optical signal to noise ratio.

Light rays emitted from the light source 22 at the critical angle in the optically clear material 34 are refracted at the sensor surface to 90° from normal 46 in the water such that the light projected into the water or the radiance distribution 48, FIG. 1, is about 180°. Light scattered in the direction of the light detector 24 is also refracted at the water surface such that the acceptance angle for the light detector or the irradiance distribution 50 is also about 180°. Thus the optically clear material 34 in the cavity 30 forms an optical element which substantially increases the angular range of projected light into the water from the range of angles emitted by the light source 22, and the optically clear material in the cavity 32 forms an optical element for gathering light from a substantially larger acceptance angle in the water than the acceptance angle of the light detector 24. Since both the radiance distribution 48 and the irradiance distribution 50 are about 180 ° or some what less than 180°, forward scattered light, back scattered light, and multiple scattered light are all included in the measurement made by this light scattering sensor. The measurement of forward scattered light, back scattered light and multiple scattered light from particles in water, preferably at nearly all angles, distinguishes this light scattering sensor design from other prior art light scattering sensors. The advantage of this design is simply that a higher signal to noise ratio is achieved by detecting more light scattered from the particles in water.

Figure 1A:
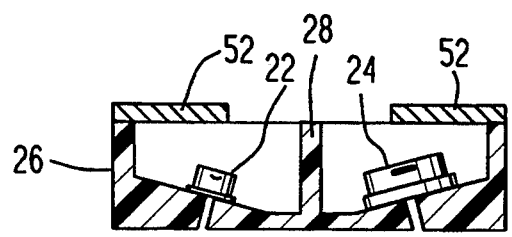
FIG. 1A is similar to FIG. 1 but showing a variation of the invention.

Some conventional light sources are unable to project angular ranges of radiance distribution sufficient to produce a radiance distribution of 180° in water, even with the aid of the clear refracting element in cavity 30, and/or some conventional light detectors do not have sufficient angular ranges of acceptance to provide irradiance acceptance from the water at angles close to 0° or 180°, even with the aid of the clear refracting element in cavity 32. Also the radiance distribution for some light sources can have reduced intensity at angles near the limits of their distribution range and the irradiance distribution of some light detectors can have reduced sensitivity at angles near their limits of acceptance. As shown in FIG. 1A, the light sources 22 can be mounted in a tilted condition so as to maximize the radiance intensity projected above the light detectors 24, and the light detectors 24 can be mounted in a tilted condition so as to maximize the sensitivity to light rays scattered from above the light sources 22. Furthermore a mask 52 can be placed over an outer portion of the range of light projection from the light source 22 and/or over an outer portion of the range of light acceptance of the light detector 24 so as to the limit the projected radiance distribution and/or the received irradiance distribution to respective smaller angles in certain circumstances, for example in relatively clear water, to avoid reflections from other objects or to otherwise limit the effective back scattering region.

The minimum light path length in water is set by the width of the light stop 28. Minimizing the light path length in water is the key to measuring very high particle concentrations. It has been determined experimentally that a light stop width of 2.5 millimeters or less permits the linear measurement of suspended particle concentrations up to 3 or 4 g/l.

The particle sensing region or sensing volume 54, FIG. 2, or the volume from which light is scattered and detected, will be controlled by several parameters such as particle concentration, particle size distribution, index of refraction of the particles, wavelength, volume scattering function, reflection losses, transmission and absorption of the water, etc. Because of this, the sensitive volume for this light scattering sensor design is not easily defined. Fortunately, it has been determined experimentally that it is not necessary to define the sensitive volume of the light scattering sensor to achieve wide dynamic range with linear response.

The light source or light sources 22 as shown in FIG. 1, are preferably conventional light emitting diodes with peak radiated power in the near infrared region of the light spectrum, 880 nm. Alternatively, the light source 22 can be any number of coherent or non-coherent light emitters in the infrared or visible portion of the spectrum.

The light detector 24 is also preferably a conventional silicon photodiode that includes a visible light blocking filter and responds linearly to incident irradiance. Alternatively, the light detector 24 can be multiple photo diodes or any of a number of photosensitive devices responsive to incident irradiance in the infrared or visible portion of the spectrum.

Figure 4:
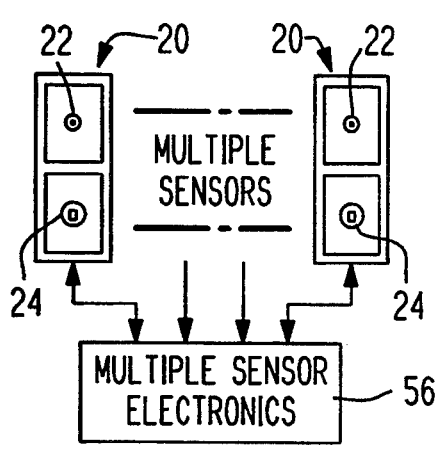
FIG. 4 is a top plan view of multiple light scattering sensors shown in FIG. 1 arranged in a planar array.

Multiple light scattering sensors 20 can be used in arrays to provide spatial data for suspended particle concentrations in water. FIG. 4 shows a linear array configured with multiple sensor electronics 56.

Figure 5:
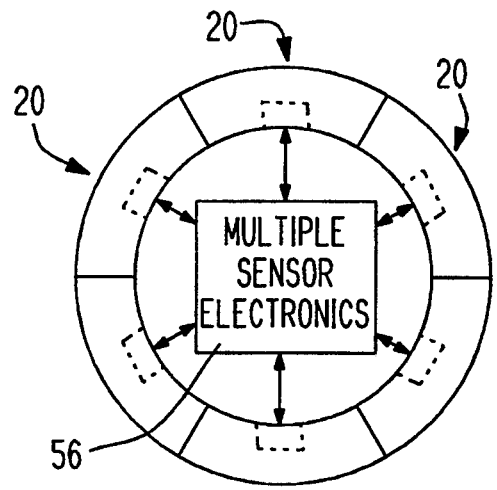
FIG. 5 is an end view of multiple light scattering sensors shown in FIG. 1 arranged in a cylindrical array.

Sensors can be constructed to operate at any of a variety of wavelengths using LED's emitting radiation at a given wavelength, and a light detector equipped with an optical filter which passes that wavelength. By combining several sensors at different wavelengths and with appropriate calibration of the sensors, spectral light scattering can be measured. FIG. 5 shows how such a multi-sensor array with spectral capability could be physically implemented in a cylindrical probe.

Figure 6:
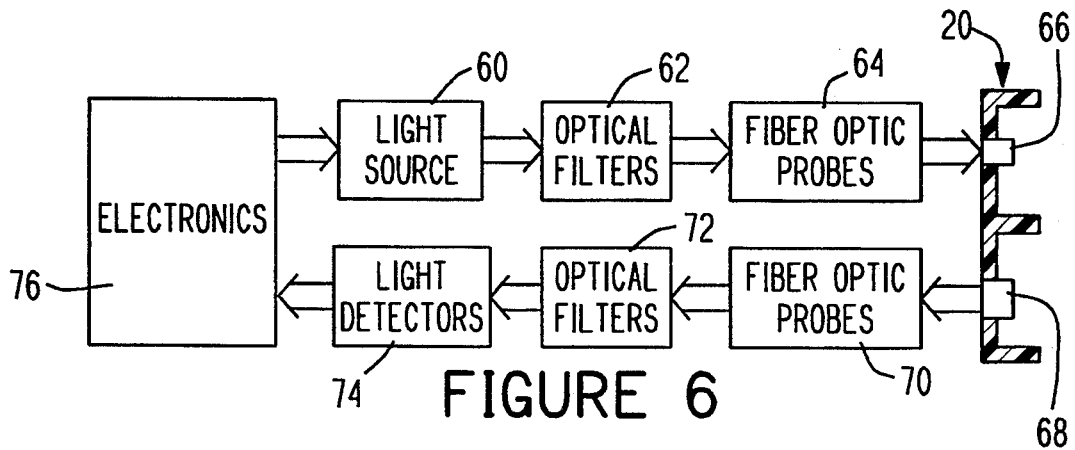
FIG. 6 is a block diagram showing the sensor of FIG. 1 configured to obtain spectral light scattering data.

Alternatively, a single white light source used in conjunction with optical filters and a light detector could also be used to produce a light scattering sensor operating at any of a variety of wavelengths. FIG. 6 shows one possible implementation of this idea using fiber optic probes. By using a number of optical filters at different wavelengths, this idea could be used to provide spectral light scattering measurements. White light from source 60 is separated into respective beams which are filtered by respective narrow band pass filters 62 into corresponding wavelength bands which are passed by fiber optic probes 64 to light emitters 66. Light acceptors 68 receive scattered radiation which is passed by fiber optic probes 70 to spectral filters 72 forming respective wavelength bands passed to corresponding light detectors 74. Energization of the light source 60 and readout of the signals from the light detectors 74 are performed by electronics circuit 76. Other arrangements of light sources, light detectors, optical filters, optical fibers and electronic designs are possible as well and could provide spectral light scattering measurements of suspended particulate matter in water using the basic scattering sensor design shown in FIG. 1.

Figure 7:
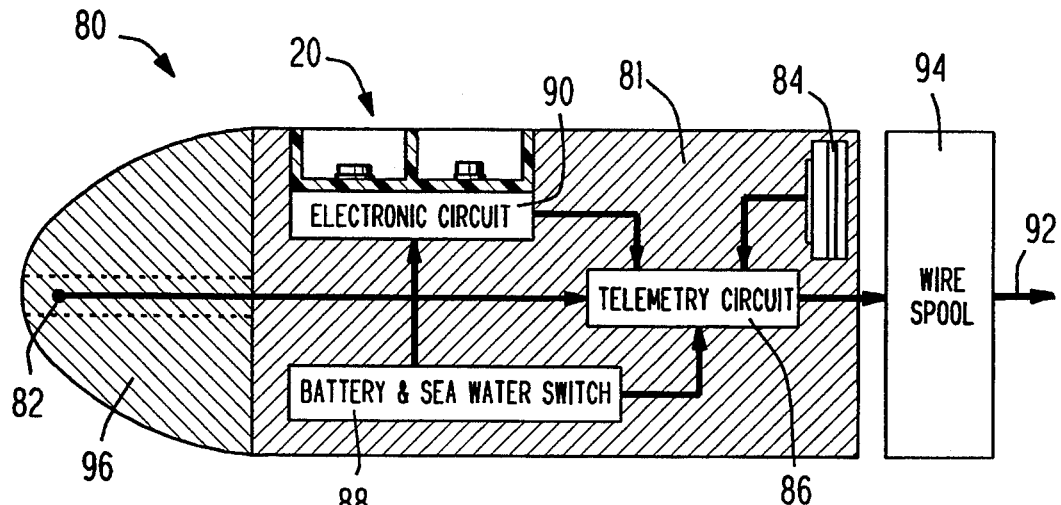
FIG. 7 is a sectional view of an expendable probe containing the light scattering sensor of FIG. 1.

Since the light scattering sensor 20 can be produced at low cost it can be used in both expendable or non-expendable applications. In FIG. 7 the light scattering sensor 20 is installed in the side of an expendable probe 80 used to obtain vertical profiles of suspended particle concentrations in natural waters. The sensor 20 is designed to have the same radius of curvature as the cylindrical housing 81 providing for good hydrodynamic design. The expendable probe, in addition to an electronic circuit 90, includes a temperature sensor 82, an optional pressure sensor 84, telemetry circuit 86 and a battery with a water switch 88 for providing power to the circuits 86 and 90 when the device is in the water. The telemetry circuit is a conventional circuit for multiplexing various signals, converting the signals to frequency modulated signals and transmitting the signals over wire 92 being unwound from a wire spool 94 as the device falls through the water column. A ballast at weight 96 at the front end of the probe 80 together with a rear fin (not shown) are used to set the probe drop rate in the water being tested. The probe 80 can be used in numerous applications where either the detection or measurement of suspended particle concentrations in water is required. Deployed from a ship the wire 92 is connected to receiving and monitoring circuitry (not shown) in the ship. Deployed from a submarine either upwards or downwards in the water the wire 92 is connected to receiving and monitoring circuitry (not shown) in the submarine. Deployed from a aircraft the wire 92 is connected to a VHF transmitter (not shown) suitably floated on the sea surface for transmitting the telemetry data to receiving and monitoring circuitry on the aircraft.

Figure 8:
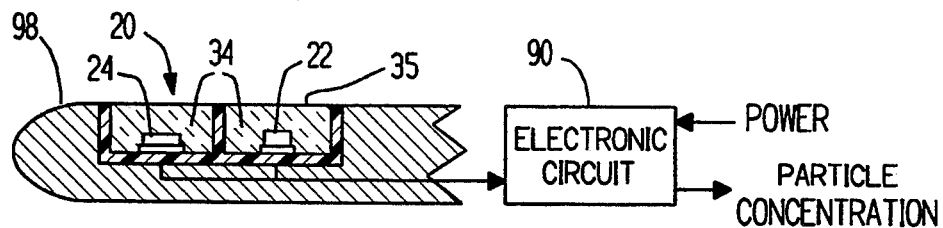
FIG. 8 is a sectional view of an non-expendable probe containing the light scattering sensor of FIG. 1.

In FIG. 8, the light scattering sensor 20 is mounted in the side of a non-expendable probe 98 that can be used for a number of applications where a measurement of the suspended particle concentration in water is desired. The optically clear material 34 having a flat or curved surface 35 that is flush with the plane or curvature of the probe surface enables the sensor to be installed in the side of the probe without disturbing the hydrodynamic characteristics of the device. The optically clear material 34 also maintains the alignment of the LED 22 and detector 24 in the probe even under severe shock that can be encountered in an oceanic environment. The result is a sensor that has good calibration stability for both laboratory and field use.

Figure 9:
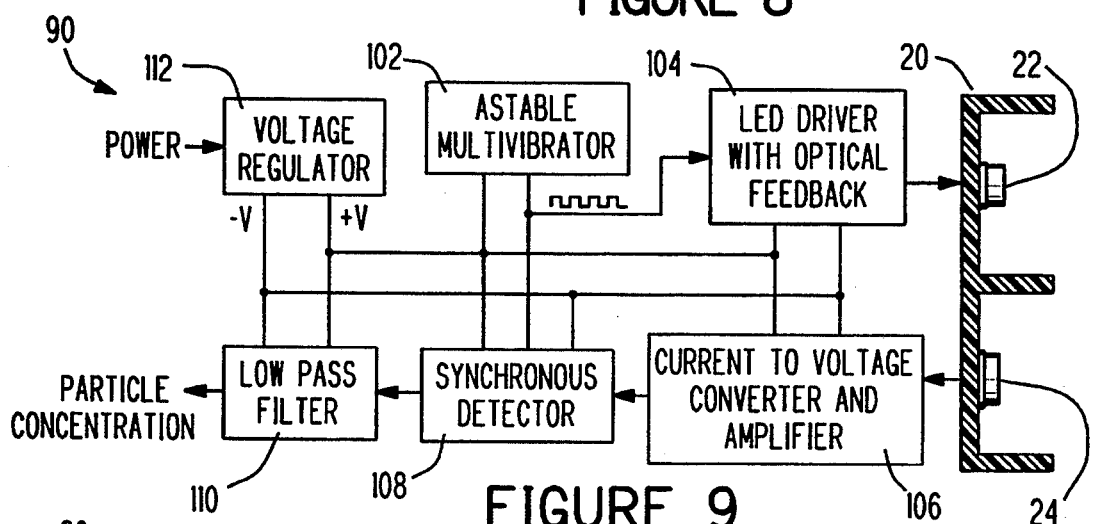
FIG. 9 is a block diagram showing the electronics circuitry used with the light scattering sensor of FIG. 1.

The conventional electronic circuit 90 for the light scattering sensor shown in FIG. 9 employs optical stabilization for the modulated light source and synchronous detection of the light scattering signal detected by the light detector. Optical stabilization of the light source makes it insensitive to environmental temperature changes. Synchronous detection was chosen for this design because it has historically been used to measure low level signals with light sensitive devices. Using this technique, it is possible to separate narrow band signals from interfering noise with high resolution; 100 db signal to noise ratio is possible. Taking advantage of this high signal to noise ratio also allows for the design of a light scattering sensor where light source power can be minimized. To achieve the electronic signal to noise ratio necessary to measure the very low level light scattering signals careful attention must be paid to circuit design. Shielding of the light detector is necessary to avoid capacitive coupling from the light source circuitry to the light detector circuitry. Good analog and digital grounding is also essential as well as proper power supply bypassing to obtain low signal to noise ratio. Chopper stabilized operational amplifiers are used to obtain very low offset voltages at the high gains needed to measure low suspended particle concentrations in water.

The design of the electronic circuit 90 shown in FIG. 9 is explained as follows: An astable multivibrator 102 produces a square wave to the LED driver circuit 104 that turns the LED 22 on and off at a rate that is not an odd or even multiple of 60 Hz such as 450 Hz or 930 Hz to avoid interference caused by power line frequency and or fluorescent lights. The LED driver circuit 104 includes optical feedback stabilizing the light output during water temperature changes. The output of the light detector 24 is amplified by a current to voltage converter and is capacitor coupled to the amplifier 106. Capacitor coupling passes the AC. signal resulting from received scattered light but blocks the DC signal produced by ambient light; this makes the sensor insensitive to ambient light. The amplifier 106 AC signal output is then synchronously rectified, (converted to DC) by the synchronous detector 108, which is controlled by the signal from the square wave generator 102. Low pass filter 110 removes higher frequency components in the synchronously rectified signal at the output of the synchronous detector 108 to produce a DC voltage proportional to the particle concentration in the water being tested. Voltage regulator circuit 112 generates and filters the voltages employed in the electronic circuit from the input power.

Figure 10:
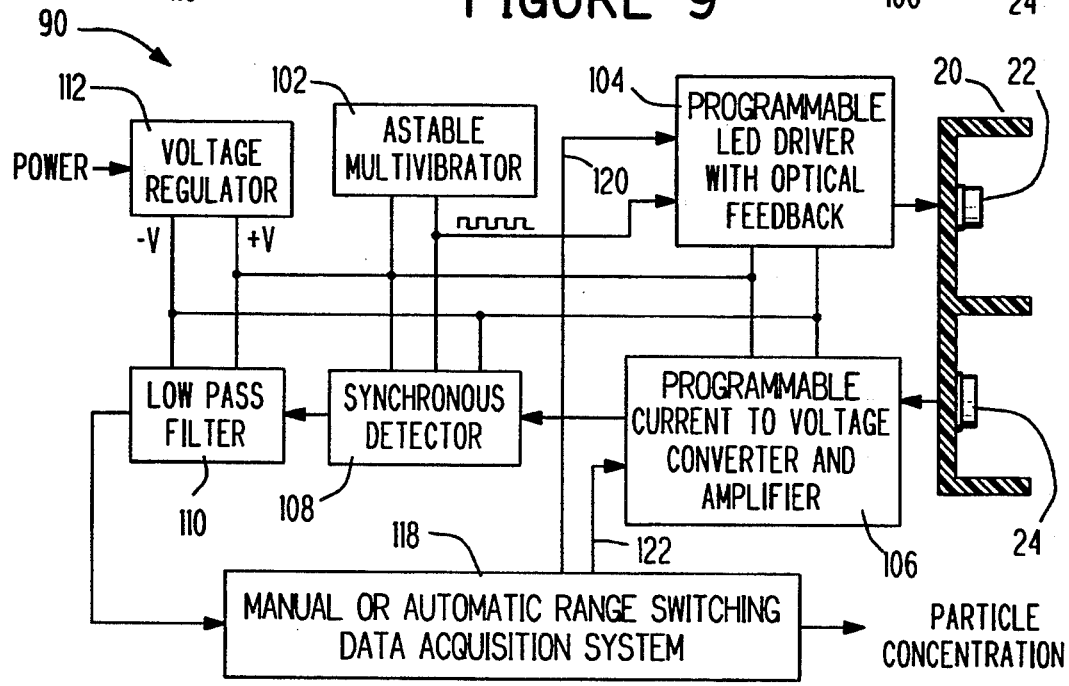
FIG. 10 is a block diagram showing how the electronics circuitry shown in FIG. 9 can be modified to incorporate manual or automatic range switching.

Practical electronic amplification circuits are limited to voltage ranges of about three or four orders of magnitude which is sufficient for most applications of the scattering sensor. When it is necessary to cover six orders of magnitude of particle concentrations, appropriate LED power and receiver gain switching using a data acquisition system will be employed as shown in FIG. 10. To achieve large dynamic range the basic electronic circuit 90 is modified to allow control of light source 22 power output and light detector 24 amplification using a conventional data acquisition system. The data acquisition system 118 is either manually or automatically controlled. The data acquisition system 118 with output 120 controls LED drive circuit 104 setting light source 22 power output. Light detector amplification circuit 106 is controlled by output 122 of the data acquisition system 78 setting appropriate receiver gain. Suspended particle concentrations in water over the range of 1 g/l to greater than 1 g/l can then be measured and recorded. Output from the data acquisition system can be analog or digital. The suspended particle concentration data can be used to control other devices or processes, displayed for real time analysis and/or recorded.

Logarithmic amplifier arrangements, or multiple sensors 20 with different sensitivities, arranged as shown in FIG. 4 or FIG. 5, can also be used to measure the large dynamic range of suspended particle concentrations in water.

Figure 11:
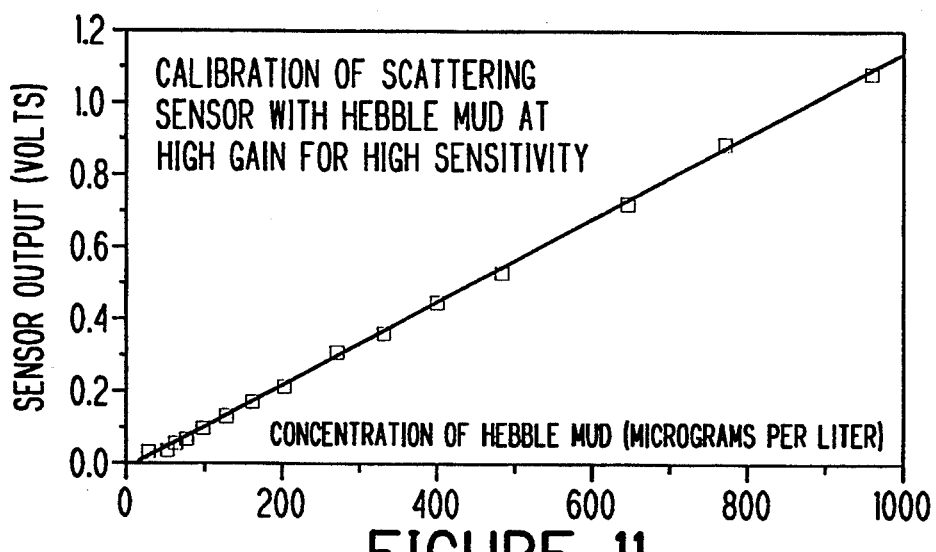
FIG. 11 is a graph showing laboratory calibration of the light scattering sensor of FIG. 1 for low concentrations of suspended particulate material.
Figure 12:
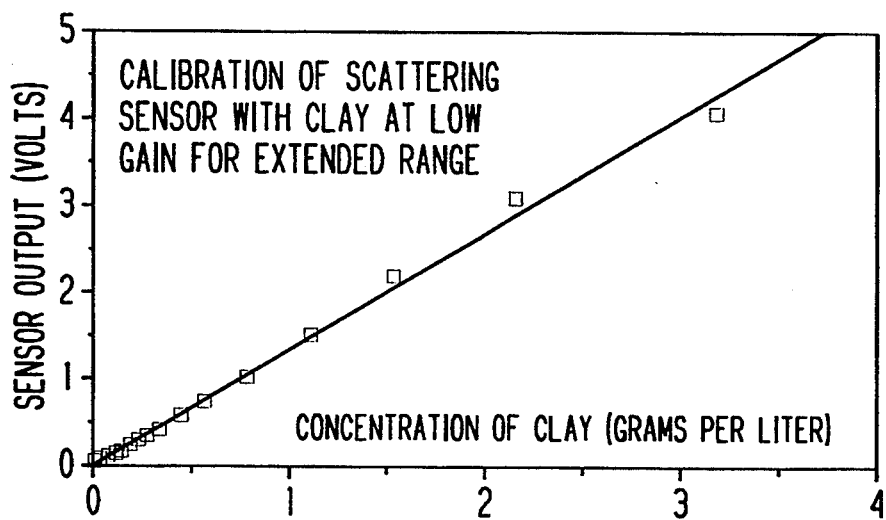
FIG. 12 is a graph showing laboratory calibration of the light scattering sensor of FIG. 1 for high concentrations of suspended particulate material.

FIGS. 11 and 12 are laboratory calibration data showing the light scattering sensor output for various concentrations of particle suspensions of Hebble deep sea mud and common clay. The calibration with Hebble deep sea mud in FIG. 11 was made with high linear gain and shows that the sensor is capable of 1 millivolt per microgram per liter sensitivity. In FIG. 12, the calibration with clay at low gain shows that the sensor is capable of linearly measuring concentrations as high as 3 grams per liter. Thus the sensor in accordance with the invention has an extraordinary linear range that allows it to measure sediment concentrations over more than 6 orders of magnitude.

Figure 13:
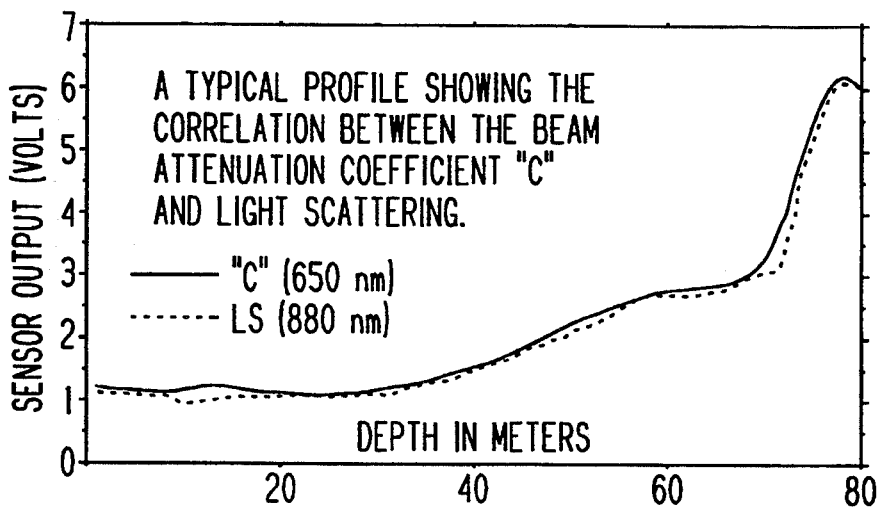
FIG. 13 is a graph of a typical profile taken in natural water with the light scattering sensor of FIG. 1 showing the correlation between the beam attenuation coefficient "C" and light scattering.

FIG. 13 shows a typical correlation that can be expected between the beam attenuation coefficient "c" and light scattering data. The profile shown was taken in fresh water where both organic and inorganic particles are present in the water column. Laboratory data (not shown) shows a similar correlation when the light scattering sensor data is compared with light transmission data.

To summarize, a light scattering sensor has been designed that maximizes the radiance distribution of the light source and the irradiance distribution of the light detector and minimizes the light path length in water. This in conjunction with very good signal to noise ratio, both optical and electronic, has resulted in the design of a light scattering sensor with extraordinary performance. Linear response over a wide dynamic range, 1 $\mu g/l$ to 3 g/l has been achieved for the measurement of suspended particle concentrations in water.

Since many modifications, variations and changes in detail can be made to the above described light scattering sensor without departing from the scope and spirit of the invention, it is intended that the above description and the accompanying drawings be interpreted as only illustrative of the described embodiment and not as limiting the invention as defined in the following claims.

What we claimed is:

1. A light scattering sensor that detects forward scattered light, back scattered light and multiple scattered light to measure suspended particle concentrations in water, comprising:
   a support;
   a light source mounted on the support so as to radiate light radiation into water at all angles within a first angle of radiance distribution;
   a light detector mounted on the support so as to receive light radiation from the water at all angles within a second angle of irradiance distribution; and
   a light stop mounted between the light source and the light detector to block any direct transmission of light from the light source to the light detector;
   said first and second angles defining a particle sensing region for sensing forward scattered light, back scattered light and multiple scattered light.

2. A light scattering sensor as claimed in claim 1 wherein the light source radiates light into the water at nearly all angles between 0° and 180°, and the light detector receives light radiation from the water at nearly all angles between 0° and 180°.

3. A light scattering sensor as claimed in claim 1 wherein the light source is mounted in a cavity on a planar support and the light source is encapsulated in an optically clear material in the cavity; said light source being spaced from the light stop at the critical angle of internal reflection for water and the encapsulation material at the edge of the light stop such that the light source radiance distribution transmitted into the water is maximized above the light stop via refraction at the water interface.

4. A light scattering sensor as claimed in claim 1 where the light detector is mounted in a cavity on a planar support and the light detector is encapsulated in an optically clear material in the cavity and the light detector is located at the critical angle of internal reflection for water and the encapsulation means relative to the edge of the light stop so that the light detector irradiance distribution is maximized via refraction at the water interface at the light stop permitting nearly all light scattered from suspended particles in water in the direction of the light detector to be detected.

5. A light scattering sensor as claimed in claim 1 wherein the light stop has a width of about 2.5 mm or less so that the light scattering sensor has a very short light path length in water.

6. A light scattering sensor as claimed in claim 1 wherein the planar support has cavities in which the light source and the light detector are mounted and which are filled with an optically clear epoxy.

7. A light scattering sensor as claimed in claim 1 wherein the support includes a pair of planarly arranged cavities in which the light source and the light detector, respectively, are mounted; said light stop being formed by a common wall between the pair of cavities; optically clear encapsulation material for the light source and the light detector; said optically clear encapsulation material having an index of refraction substantially greater than the index of refraction of water, so that light radiation emitted from the light source and received by the light detector is refracted at the water and the optically clear encapsulation material.

8. A light scattering sensor as claimed in claim 1 wherein the light source is an infrared light emitting diode and the light detector is a sunlight blocked photosensitive device.

9. A light scattering sensor as claimed in claim 1 wherein the light source output is controlled and temperature stabilized using optical feedback means.

10. A light scattering sensor as claimed in claim 1 wherein the light source is a visible light emitting diode, and the light detector is a photosensitive device with or without an optical filter.

11. A light scattering sensor as claimed in claim 1 including multiple wavelength light source means employed to measure spectral light scattering from suspended particle concentrations in water.

12. A light scattering sensor as claimed in claim 1 including multiple light scattering sensors with respective means for limiting response at different wavelengths to measure spectral light scattering from suspended particle concentrations in water.

13. A light scattering sensor as claimed in claim 1 wherein the light scattering sensor includes means for producing a linear response over a measurement range for suspended particle concentration in water from 1 µg/l to 3 g/l.

14. A light scattering sensor as claimed in claim 1 including means for controlling the light scattering sensor light source power output to obtain a linear measurement range for suspended particle concentrations in water from 1 µg/l to 3 g/l.

15. A light scattering sensor as claimed in claim 1 including receiver means for amplifying a signal from the light detector, and means for controlling the amplification of the receiver to obtain a linear measurement range for suspended particle concentrations in water from 1 µg/l to 3 g/l.

16. A light scattering sensor as claimed in claim 1 wherein multiple light scattering sensors are used to obtain a linear measurement range for suspended particle concentrations in water from 1 µg/l to 3 g/l.

* * * * *